(12) United States Patent
Kinoshita et al.

(10) Patent No.: US 8,771,246 B2
(45) Date of Patent: Jul. 8, 2014

(54) WEARING ARTICLE AND METHOD OF FOLDING UP THE SAME

(75) Inventors: Akiyoshi Kinoshita, Kagawa (JP); Natsuko Aoyagi, Kagawa (JP); Kayoko Tanaka, Kagawa (JP); Yasuhiko Kenmochi, Kagawa (JP)

(73) Assignee: Unicharm Corporation, Ehime (JP)

(*) Notice: Subject to any disclaimer, the term of this patent is extended or adjusted under 35 U.S.C. 154(b) by 333 days.

(21) Appl. No.: 12/992,347

(22) PCT Filed: Mar. 23, 2009

(86) PCT No.: PCT/JP2009/055600
§ 371 (c)(1),
(2), (4) Date: Feb. 11, 2011

(87) PCT Pub. No.: WO2009/139225
PCT Pub. Date: Nov. 19, 2009

(65) Prior Publication Data
US 2011/0209269 A1   Sep. 1, 2011

(30) Foreign Application Priority Data

May 14, 2008  (JP) .................. 2008-127707

(51) Int. Cl.
| A61F 13/15 | (2006.01) |
| A61F 13/20 | (2006.01) |
| A61F 13/56 | (2006.01) |
| A61F 13/58 | (2006.01) |
| A61F 13/49 | (2006.01) |

(52) U.S. Cl.
CPC ........... *A61F 13/5644* (2013.01); *A61F 13/581* (2013.01); *A61F 13/49* (2013.01)
USPC ..................... 604/385.01; 604/358

(58) Field of Classification Search
CPC ............ A61F 13/5512; A61F 13/5515; A61F 13/5622; A61F 13/5638; A61F 13/5644; A61F 13/58; A61F 13/581; A61F 13/60; A61F 13/622; A61F 13/625; A61F 13/627
USPC ...................... 604/385.01, 385.201, 389–391
See application file for complete search history.

(56) References Cited

U.S. PATENT DOCUMENTS 5,759,181 A     6/1998 Sayama et al.
6,302,871 B1 * 10/2001 Nakao et al. ............. 604/385.13
(Continued)

FOREIGN PATENT DOCUMENTS

JP     01-156502    6/1989
JP     09-103447    4/1997
(Continued)

OTHER PUBLICATIONS

International Search Report from corresponding PCT application No. PCT/JP2009/055600 dated Jun. 23, 2009, 4 pages.

*Primary Examiner* — Philip R Wiest
*Assistant Examiner* — Benjamin Klein
(74) *Attorney, Agent, or Firm* — Brinks Gilson & Lione

(57) ABSTRACT

A wearing article adapted to be folded up as compactly as possible in a sanitary manner utilizing the component of the wearing article itself. The wearing article having front and rear waist regions that include a first pair of lateral zones opposed to each other in a transverse direction X and extending in a longitudinal direction Y and a second pair of lateral zones opposed to each other in the transverse direction X and extending in the longitudinal direction Y, respectively. An inner sheet is provided in the respective first lateral zones with mount members defining first engagement regions and hook elements of mechanical fastener are attached to a chassis via these mount members. The respective second lateral zones of the inner sheet define second engagement regions and provided with loop elements attached thereto. The front and rear waist regions are provided with waist elastic members attached thereto under tension so as to extend in the transverse direction X. The mount members are formed by fibrous sheet adapted to be engaged with the hook members and thereby define third engagement regions.

2 Claims, 3 Drawing Sheets

(56) References Cited

U.S. PATENT DOCUMENTS

| | | | |
|---|---|---|---|
| 6,911,023 B1 * | 6/2005 | Hamilton et al. | 604/387 |
| 6,953,452 B2 * | 10/2005 | Popp et al. | 604/391 |
| 7,527,617 B2 * | 5/2009 | Shimada et al. | 604/389 |
| 2001/0053903 A1 * | 12/2001 | Shingu et al. | 604/385.31 |
| 2006/0218700 A1 * | 10/2006 | Uda | 2/400 |

FOREIGN PATENT DOCUMENTS

| | | |
|---|---|---|
| JP | 2002-000648 | 1/2002 |
| JP | 2002-532147 | 10/2002 |
| JP | 2003-144493 | 5/2003 |
| WO | WO 00/35398 | 6/2000 |

* cited by examiner

WEARING ARTICLE AND METHOD OF FOLDING UP THE SAME

RELATED APPLICATION

This application is a 35 U.S.C. §371 national phase filing of International Patent Application No. PCT/JP2009/055600, filed Mar. 23, 2009, through which and to which priority is claimed under 35 U.S.C. §119 to Japanese Patent Application No. 2008-127707, filed May 14, 2008.

TECHNICAL FIELD

The present invention relates to wearing articles and more particularly to wearing articles such as disposable diapers, toilet training pants, incontinent briefs, menstruation knickers/panties or diaper covers and a method to fold up such wearing articles.

RELATED ART

A disposable diaper of which the opposite lateral zones are detachable is known, for example, from the disclosure of Publication of JP 2002-532147 T (PATENT DOCUMENT 1). According to the disclosure of this PATENT DOCUMENT 1, the diaper comprises a chassis including a front region, a rear waist region, a crotch region and having an inner side facing the wearer's skin and an outer side facing a garment worn by the wearer, and hook elements and loop elements attached to transversely opposite lateral zones of the front and rear waist regions. Specifically, transversely opposite lateral zones of the front waist region are provided on the outer side facing the garment with the loop elements and the transversely opposite lateral zones of the rear waist region are provided with the hook elements so that these may be engaged together to put the diaper into a pant-shape. The crotch region is provided with an absorbent structure serving to absorb bodily fluids.

[PATENT DOCUMENT 1] JP 2002-532147 T

DISCLOSURE OF THE INVENTION

Problem to be Solved by the Invention

For disposal of the used diaper, it is desired to fold up or roll up the used diaper not only in a sanitary manner but also as compactly as possible. To keep the used diaper in such a compactly folded up or rolled up condition, it is contemplated to use a dedicated means such as pressure-sensitive adhesive tapes attached to the diaper separately. However, such dedicated means separately added should result in a corresponding increase of the manufacturing cost. Nonetheless, it is seriously desired to incorporate some kind of means to keep the used diaper to be compactly folded up.

It is an object of the present invention to provide a wearing article adapted to be folded up as compactly as possible in a sanitary manner utilizing the component of the wearing article itself.

Measure to Solve the Problem

The present invention includes a first aspect relating to a wearing article and a second aspect relating to a method of folding up the used wearing article. The object set forth above is achieved, according to the present invention on its first aspect, by an improvement in a wearing article comprises a chassis having longitudinal direction and transverse direction, inner side facing the wearer's skin and outer side facing a garment worn by a wearer, a first waist region defined by one of front and rear waist regions, a second waist region defined by the other of the front and rear waist regions and a crotch region extending between the first and second waist regions, and a mechanical fastener including first engagement regions formed in a pair of first lateral zones of the first waist region which are opposed to in the transverse direction and extending in the longitudinal direction and having a mechanical fastener function and second engagement regions formed in a pair of second lateral zones of the second waist region which are opposed to each other in the transverse direction and extending in the longitudinal direction and having a mechanical fastener function and adapted to be detachably engaged with the first engagement regions, wherein the first engagement regions include hook elements formed on the outer sides of the first lateral zones facing the garment and the second engagement regions include loop elements formed on the inner sides of the second lateral zones facing the skin of wearer.

The improvement according to a first aspect of the present invention is characterized in that the wearing article further comprises third engagement regions having mechanical fastener function and adapted to be detachably engaged with the first engagement regions, the third engagement regions being at least formed on respective inner sides of the first lateral zones facing wearer's skin so that the first engagement region formed on outer side of one of the first lateral zones facing wearer' garment is be able to engaged with the third engagement region formed on inner side of other of the first lateral zones facing the skin of the wearer.

According to one preferred embodiment of the first aspect, the first lateral zones include mount members via which the hook elements are attached to the first lateral zones, and each of the mount members respectively has an inner side of the mount member facing the skin of the wearer and an outer side the garment and formed by a fibrous sheet so that at least the inner side of the mount member facing skin of the wearer is engageable with the hook elements and thereby defines the third engagement region.

According to another preferred embodiment of the first aspect, the chassis comprises an inner sheet defining the inner side facing skin of the wearer and an outer sheet defining the outer side the garment, and the hook elements are formed on the outer sheet and the loop elements are formed on the inner sheet, thereby the inner sheet being formed of a fibrous sheet adapted to be engaged with the hook elements so as to define the third engagement regions.

According to still another preferred embodiment of the first aspect, the hook elements are formed on the first lateral zones so as to extend substantially full dimensions of the first lateral zones in the longitudinal direction.

According to yet another preferred embodiment of the first aspect, the first waist region provided with the hook elements are elasticized in the transverse direction.

A second aspect of the present invention relates to a method of folding up the used diaper according to claim 1. The second aspect of the present invention comprising the steps of detaching the first and second waist regions from each other along the first and second engagement regions, placing the first and second waist regions upon each other with the outer sides thereof exposed outside, folding back one of the first lateral zones onto the second waist region, folding back other of the first lateral zones onto the second waist region so that the first engagement region defined in one of the first lateral zone is engaged with the third engagement region defined on the inner side of the first engagement region defined in the other of the first lateral zones and thereby keeping the used diaper in its folded up condition.

One preferred embodiment of the second aspect further includes folding back the crotch region onto the second waist region before the step of folding back the one and the other of the first lateral zones onto the second waist region together with associated the second lateral zones, and interleaving the crotch region between the one and the other of the first lateral zones folded back together with the associated second lateral zones and the second waist region.

Effect of the Invention

The wearing article according to the first aspect of the present invention includes, in addition to the first and second engagement regions in which the first pair of lateral zones and the second pair of lateral zones can be detachably engaged together, the third engagement regions formed on the respective inner sides of the first pair of lateral zones so that these third engagement regions can be engaged with the first engagement regions. As will be understood from the description hereinafter, these third engagement regions are used to fold up the used wearing article compactly in a sanitary manner and may be formed of a fibrous sheet adapted to be engageable with the hook elements. In other words, the fibrous sheet such as a nonwoven fabric conventionally defining the inner side of the disposable diaper and/or the side edges (ear regions) of the waist regions can be directly used as the third engagement regions. In this way, it is no more necessary to provide separate means or members to form the third engagement regions and thereby an increase of cost due to such separate means or members can be avoided. The mechanical fastener comprises hook elements and loop elements and therefore the well known "Velcro" (trademark) or "Magic Tape" (trademark) can be used as these hook elements and the loop elements.

According to the embodiment wherein the hook elements defining the first engagement regions are attached to the first lateral zones via the mount members defining the side edges (ear regions) of the chassis. In this way, the mount members can be formed by the members separately of the lateral zones of the chassis. With the arrangement in which the presence of the mount members makes the first lateral zones extend further outward in the transverse direction compared to the second lateral zones, the mount members can be easily gripped between the fingers and pulled in the transverse direction even after the first and second waist regions have been placed on each other.

According to the embodiment wherein the inner sheet defining the inner side of the chassis facing the skin of the wearer is formed of a fibrous sheet being able to be engaged with the hook elements, the regions of the inner sheet adapted to be engaged with the hook elements can define the third engagement regions. Thus none of separate members is required to define the third engagement regions.

According to the embodiment wherein the hook elements are formed on the first lateral zones so as to extend substantially full dimensions of the first lateral zones in the longitudinal direction, the hook elements are able to be engaged with the third engagement regions in a range as wide as possible and the folded up used wearing article would not be unintentionally unfolded.

According to the embodiment wherein the first waist region provided with the hook elements are elasticized in the transverse direction, the hook elements and the third engagement regions put in engagement are pulled in the transverse direction and thereby the engagement effect is made further secure. In addition, the first waist region elasticized in this manner well tightens the folded up wearing article without leaving any slack. In consequence, the used wearing article would not be unintentionally slacked and body waste would not leak out.

The method of folding up the used wearing article according to the second aspect of the invention assures the used wearing article to be compactly folded up in a sanitary manner as has been described above and to be kept in such compactly folded up condition because of such unique folded up arrangement and the third engagement regions.

According to the embodiment further including the steps of folding back the crotch region onto the second waist region before the step of folding back the one and the other of the first lateral zone onto the second waist region, and interleaving the crotch region between the pair of the first lateral zone folded back and the second waist region, it is assured to make the used wearing article to be folded up further compactly.

Figure 1:
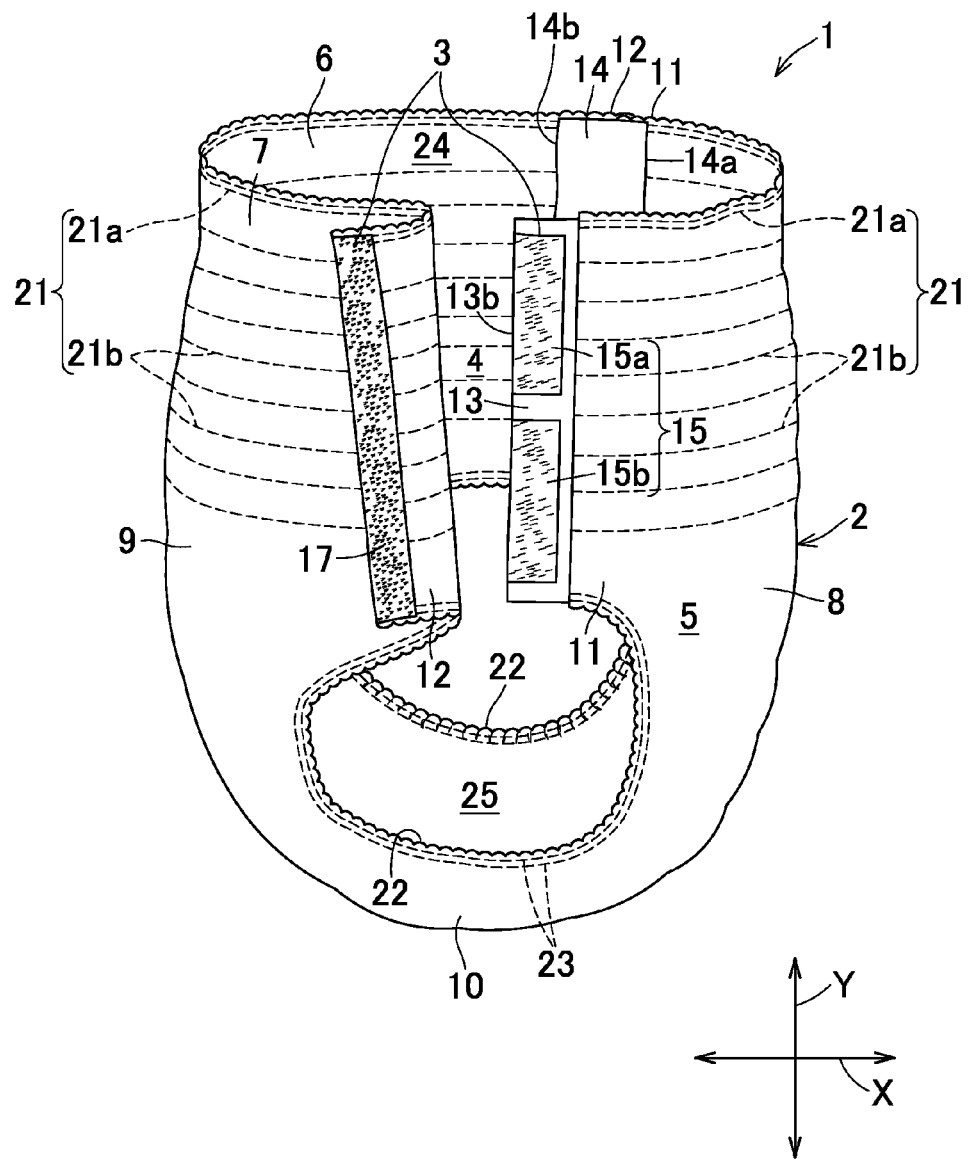
FIG. 1 is a perspective view of a disposable diaper.

IDENTIFICATION OF REFERENCE NUMERALS USED IN THE DRAWINGS 1 diaper
2 chassis
3 mechanical fastener
4 inner side facing the skin of a wearer
5 outer side facing a garment
6 inner sheet
7 outer sheet
8 front waist region
9 rear waist region
10 crotch region
11 first lateral zone
12 second lateral zone
13 mount member
14 mount member
15 hook element
16 hook element
17 loop element
18 loop element
21 waist elastic member

DETAILED DESCRIPTION OF THE PREFERRED EMBODIMENTS

Embodiment

Figure 2:
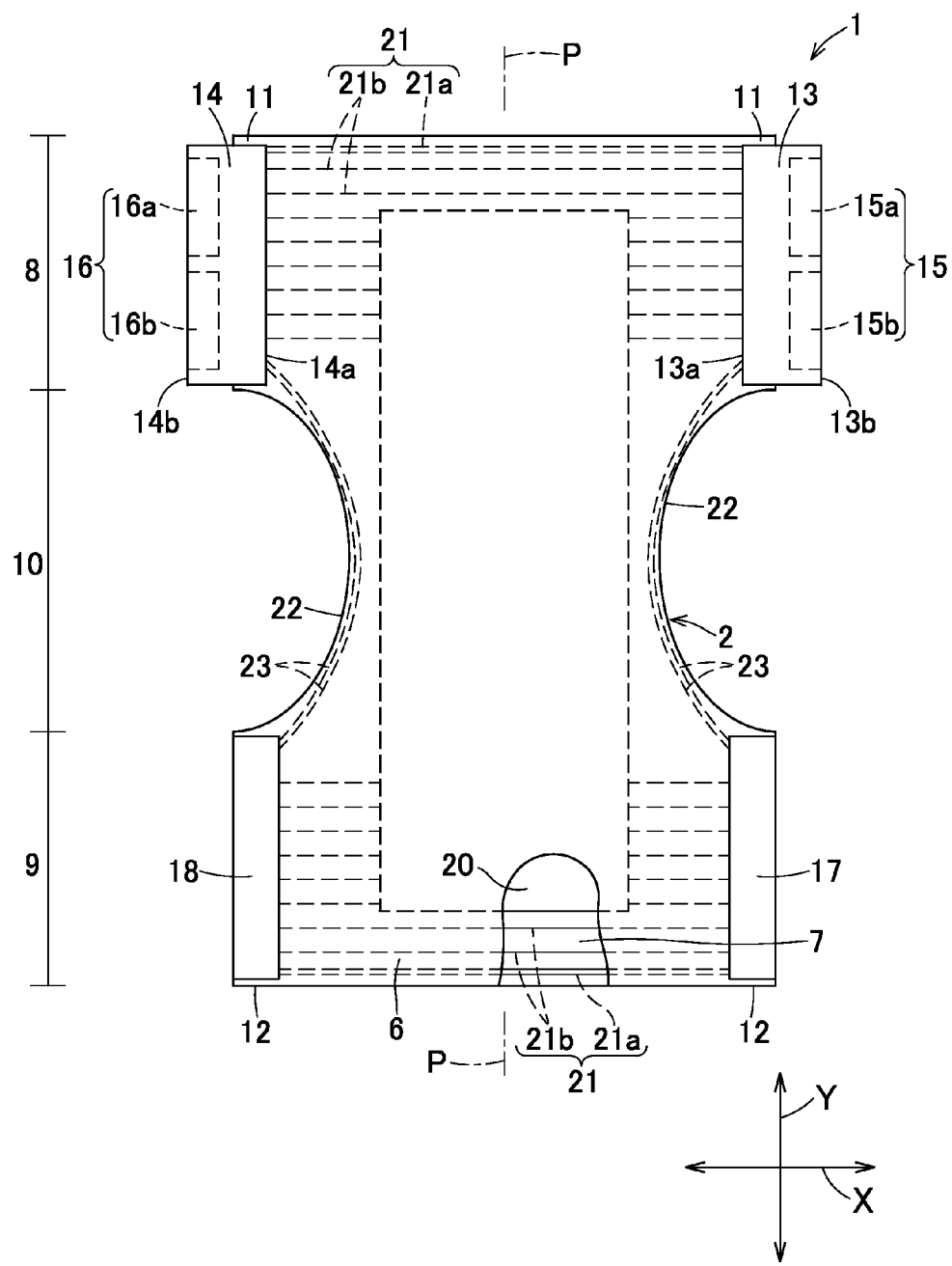
FIG. 2 is a plan view showing the diaper of FIG. 1 as has been flatly developed.
Figure 3:
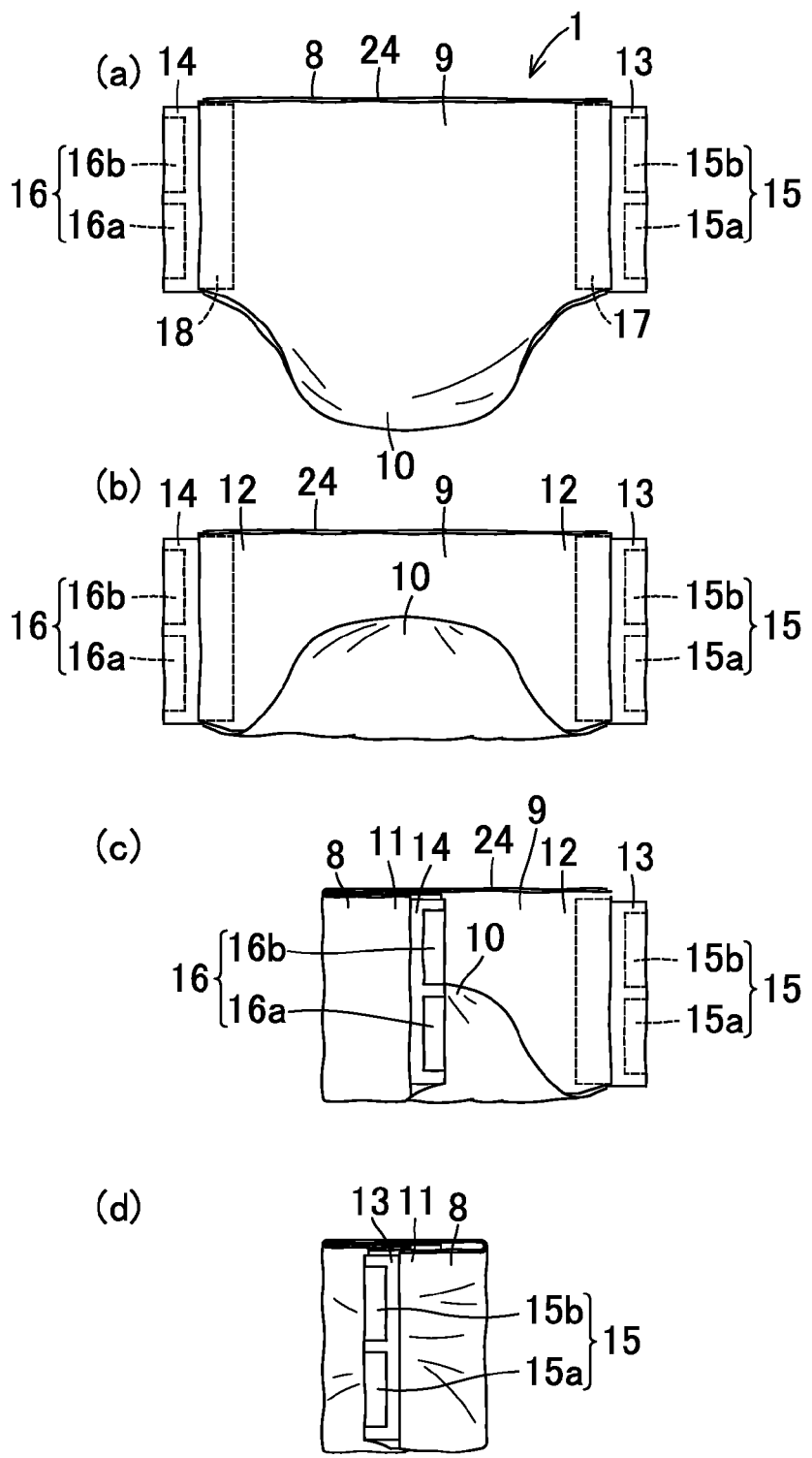
FIG. 3 is a diagram illustrating how the diaper is sequentially folded up.

FIGS. 1 through 3 illustrate a diaper for adult as one embodiment of the present invention wherein FIG. 1 is a perspective view of the diaper 1 as put on the wearer and one of opposite side edges of the diaper 1 left opened, FIG. 2 is a flatly developed plan view of the diaper 1 as partially broken away for convenience of illustration, and FIG. 3 is a diagram illustrating how the diaper 1 is sequentially folded up. As shown, the diaper 1 includes a chassis 2 having a liquid-absorbing ability and mechanical fasteners 3. The chassis 2 has a longitudinal direction Y, a transverse direction X, an inner sheet 6 defining an inner side facing the skin of the wearer, an outer sheet 7 defining an outer side facing a garment of the wearer and a liquid-absorbent core 20 sandwiched between these inner and outer sheets 6, 7. The inner sheet 6 may be formed, for example, of a liquid-pervious fibrous nonwoven fabric, the outer sheet 7 may be formed, for example, of a liquid-impervious plastic film and the liquid-absorbent core 20 may be formed, for example, from a mixture of fluff pulp and super-absorbent polymer particles. These stock materials have conventionally been used in the relevant technical field. The chassis 2 comprises a front waist region 8, a rear waist region 9 and a crotch region 10 extending between these two waist regions 8, 9.

The front waist region 8 has a pair of first lateral zones 11 opposed to each other in the transverse direction X and extending in the longitudinal direction Y while the rear waist region 9 has a pair of second lateral zones 12 opposed to each other in the transverse direction X and extending in the longitudinal direction Y. The inner sheet 6 is provided along the respective first lateral zones 11 with mount members (ear members) 13, 14, respectively, which are elongated in the longitudinal direction Y. Via these mount members 13, 14, arrays of hook elements 15, 16 constituting the respective mechanical fasteners are attached to the chassis 2 so as to form first engagement regions, respectively. It should be noted here that the first lateral zones sometimes refer to the assemblies of the first lateral zones 11 and the mount members 13, 14 collectively hereinafter in the description of the invention. Each of these mount members 13, 14 may be formed, for example, of a fibrous nonwoven fabric having one of the side edges 13a or 14a bonded to the associated first lateral zone 11 of the inner sheet 6 by adhesives, thermal bonding or ultrasonic bonding means and the other side edge 13b or 14b extending outward from the associated first lateral zone 11 in the transverse direction X. These portions of the mount members 13, 14 extending outward are provided on respective outer sides facing a garment worn by the wearer with the arrays of hook elements 15, 16 bonded thereto by adhesives, thermal bonding or ultrasonic bonding means. The arrays of hook elements 15, 16 are respectively divided in upper and lower sub-arrays 15a, 16a and 15b, 16b and each pair of the upper and lower sub-arrays is spaced apart from each other.

The mount members 13, 14 respectively have dimension of substantially the same as the dimension of the first lateral zones 11 as measured in the longitudinal direction Y and the arrays of hook elements extend to cover substantially over the entire area of the respective mount members 13, 14 in the longitudinal direction Y. More specifically, the arrays of hook elements 15, 16 extend in the longitudinal direction Y leaving slight spaces between ends of the mount members 13, 14 opposite in the longitudinal direction Y and the upper and lower sub-arrays 15a, 16a and 15b, 16b as well as between these upper and lower sub-arrays 15a, 16a and 15b, 16b. Initially, the front and rear waist regions 8, 9 have substantially the same dimensions in the transverse direction X. After the mount members 13, 14 have been attached to the respective first lateral zones 11 of the front waist region 8, the dimension of the front waist region 8 as measured in the transverse direction X became larger than the dimension of the rear waist region 9 as measured in the transverse direction X substantially by width dimensions of the mount members 13, 14. While differentially dimensioning the front and rear waist regions 8, 9 in the transverse direction X in this manner is preferable in the course of sequentially folding up the wearing article as will be described later, such dimensioning is not essential.

The inner sheet 6 is formed along the second lateral zones 12 of the rear waist region 9 with second engagement regions in which arrays of loop elements 17, 18 are attached to the inner sheet 6 by adhesive, thermal bond or ultrasonic bond. The arrays of loop elements 17, 18 respectively have a dimension of substantially the same as a dimension of the second lateral zones 12 of the rear waist region 9 as measured in the longitudinal direction Y and extend to cover substantially over the entire area of the second lateral zones 12 in the longitudinal direction Y. The hook elements 15, 16 and the loop elements 17, 18 are adapted to be detachably engaged one with another and, as these hook elements 15, 16 and loop elements 17, 18, "Velcro" (trademark) or "Magic Tape" (trademark) widely used in the technical field to which the present invention relates may be effectively used.

The front and rear waist regions 8, 9 are provided with waist elastic members 21 attached thereto under tension so as to extend in the transverse direction X. More specifically, these waist elastic members 21 comprise first elastic members 21a provided in the vicinity of the peripheral edge of the waist-opening and second elastic members 21b provided aside from the first elastic members 21a toward the crotch region 10. These waist elastic members 21 are sandwiched between the inner and outer sheets 6, 7 and attached to at least one of the inner and outer sheets 6, 7 by adhesives, thermal bonding or ultrasonic bonding means. The waist elastic members 21 are formed of a plurality of thread-, strand- or tape-like rubber elements wherein the second elastic members 21b are placed substantially at regular intervals in the longitudinal direction Y practically over the entire area of the front and rear waist regions 8, 9 so as to elasticize the front and rear waist regions 8, 9 in the transverse direction X. The front and rear waist regions 8, 9 elasticized in this manner ensure desired fitness of the front and rear waist regions 8, 9 to prevent bodily fluids such as urine from leaking out and at the same time to improve appearance of the article put on the wearer.

In the front waist region 8, the waist elastic members 21 extend in the transverse direction X to respective inner sides of the mount members 13, 14 without intersecting with the mount members 13, 14. The arrays of hook elements 15, 16 are placed in the respective regions of the mount members 13, 14 extending outward from the side edges of the front waist region 8 and therefore the waist members 21 do not overlap the arrays of hook elements 15, 16. In the rear waist region 9 also, the waist members 21 extend to the innermost side edges of the loop elements 17, 18 and do not intersect with these loop elements 17, 18. In this way, the arrays of hook elements 17, 18 as well as the loop elements 17, 18 are prevented from getting wrinkled under contraction of the waist elastic members 21. In consequence, a desired area of engagement can be prevented from being reduced and the engagement can be prevented from becoming unstable due to formation of wrinkles. It is assured therefore that the hook elements 15, 16 and the loop elements 17, 18 can be kept in secure engagement.

Between the first pair of lateral zones 11 and the second pair of lateral zones 12 as viewed in the longitudinal direction Y, a pair of leg side edges 22 formed in the crotch region 10 extends so as to curve toward a longitudinal center line P-P bisecting a dimension of the crotch region 10 in the transverse direction X. Along the leg side edges 22, leg elastic members 23 are attached under tension to the chassis 2. More specifically, these leg elastic members 23 are sandwiched between the inner and outer sheets 6, 7 and attached to at least one of these inner and outer sheets 6, 7 by adhesive, thermal bonding or ultrasonic bonding means. The leg elastic members 23 are formed of a plurality of thread-, strand- or tape-like rubber elements so that the leg side edges 22 may fit the thighs of the wearer under contractile force of these rubber elements and prevent bodily fluids such as urine from accidentally leaking beyond respective peripheral edges of the leg-openings. It is possible without departing from the scope of the invention to use natural rubber or synthetic rubber such as polyurethane, or to replace such natural or synthetic rubber, for example, by elasticized fibrous nonwoven fabric or plastic sheet or the other elastic members commonly used.

In such diaper 1 as has been described above, the loop elements 17, 18 may be engaged with the hook elements 15, 16 to connect the front and rear waist regions 8, 9 with each other, thereby to form a waist-opening 24 and a pair of leg-openings 25 and, in consequence, to make the diaper 1 in pull-on pant-shape. To put on the wearer this diaper 1 with its front and rear waist regions 8, 9 connected with each other, the legs of the wearer may be guided through the waist-opening 24, then through the leg-openings 25 and finally the diaper 1 may be pulled upward. Alternatively, the front and rear waist regions 8, 9 may be put on the front and rear waist regions of the wearer before the front and rear waist regions 8, 9 are connected to each other, then the hook elements 15, 16 may be engaged with the loop elements 17, 18 to connected the front and rear waist regions 8, 9 to each other and thereby to make the diaper 1 in pant-shape. In this way, such diaper 1 is selectively used as the pull-on pant-type diaper and as the open-type diaper.

In any case, the hook elements 15, 16 are divided into the upper sub-arrays 15a, 16a and the lower sub-arrays 15b, 16b and these sub-arrays may be one by one engaged with the loop elements 17, 18. In this way, operating efficiency can be improved in comparison with the case in which a series of the long hooks are engaged with the loop elements at once. In addition to improvement of the operating efficiency, the manner in which these upper sub-arrays 15a, 16a and the lower sub-arrays 15b, 16b are one by one engaged with the loop elements 17, 18 is advantageous from another viewpoint. In fact, when it is desired to correct a misalignment after engagement or when it is desired to release the engagement disengage in order to check whether urination or defecation has occurred or not, the upper or lower sub-array of hook elements may be disengaged from or reengaged with the associated portion of loop elements. Such manner of operation is easier than the manner in which the entire array of hook elements is reengaged at once with the array of loop elements.

The diaper 1 may be taken off from the wearer by disengaging the arrays of hook elements 15, 16 from the loop elements 17, 18 or taken off without such operation of disengagement as if briefs are taken off. For disposal of the used diaper 1, it is desired to fold up the used diaper 1 to a compact volume with neatness in order to prevent the body waste and its malodor from leaking out and to prevent the used diaper 1 from resulting in a bulky piece of garbage. Steps of sequentially folding up the used diaper 1 are illustrated by FIG. 3.

As seen in FIG. 3(a), in a first step, the hook elements 15, 16 are disengaged from the loop elements 17, 18, the diaper 1 is developed on a flat surface such as a bed and then the front and rear waist regions 8, 9 are lapped one on another with the outer sheet 7 outside. Referring to FIG. 3(a), the front waist region 8 lies on the remote side and the rear waist region 9 lies on the near side of the plane defined by this drawing. In a second step illustrated by FIG. 3(b), the crotch region 10 is folded back toward the waist-opening 24 onto the rear waist region 9.

After the crotch region 10 has been folded back onto the rear waist region 9, one of the first lateral zones 11 having the array of hook elements 16 is folded back together with the associated second lateral zone 12 onto the crotch region 10 as seen in FIG. 3(c). On this point, the array of hook elements 16 defines the uppermost layer. In a final step illustrated by FIG. 3(d), the other first lateral zone 11 having the array of hook elements 15 is folded back together with the associated second lateral zone 12 onto the array of hook elements 16 of the previously folded first lateral zone 11. On this point, the lateral zone 11 having the array of hook elements 15 defines the uppermost layer and the mount member 13 associated with the array of hook elements 15 comes in contact with the array of hook elements 16 on the first lateral zone 11. The mount members 13, 14 are formed of a fibrous sheet such as a nonwoven fabric, a woven fabric or a mesh fabric and adapted to be engaged with the arrays of hook elements 15, 16.

The mount member 13 extends outward beyond the second lateral zone 12 of the rear waist region 9 in the transverse direction X. Therefore the mount member 13 can be easily brought into contact with the array of hook elements 16 of the first lateral zone 11 which has previously folded. If the mount member 13 does not extend beyond the second lateral zone 12 in the transverse direction X, the second lateral zone 12 will be interposed between the mount member 13 and the previously folded lateral zone including the array of hook elements 16. Such situation will make it impossible to bring the mount member 13 into contact with the array of hook elements 16. Even in such situation, however, the second lateral zone 12 may be folded back or the mount member 13 on this second lateral zone 12 may be pulled outward in the transverse direction X to make it possible to bring the mount member 13 into contact with the array of hook elements 16. The mount member 13 extending outward beyond the second lateral zone 12 in the transverse direction X facilitates the mount member 13 to be securely held between the fingers and thereby facilitates the mount member 13 to be pulled in the transverse direction X. In this way, operation of folding up the first lateral zone 11 is facilitated.

Assumed that a nonwoven fabric is used to form the mount members 13, 14, the orientation intrinsic to a nonwoven fabric in general, particularly in association with its tensile strength, can be advantageously utilized. More specifically, the mount members 13, 14 formed of a nonwoven fabric may be attached to the diaper 1 so as to extend in the transverse direction X in which the mount members 13, 14 have the maximum tensile strength and thereby these mount members 13, 14 can be reliably protected from being damaged. While nonwoven fabric of the type widely used in the technical field to which the present invention relates principally has a random orientation, even such nonwoven fabric may have more or less significant orientation depending on the process of manufacturing. Taking account of this, the mount members 13, 14 are preferably attached to the diaper 1 so that a relatively prevailing direction of component fibers may correspond to the transverse direction X.

The hook elements 16 and the mount member 13 have been brought into contact and engagement with each other in the manner as has been described above. It is possible thereby to connect the pair of opposite first lateral zones to each other and simultaneously to keep the front and rear waist regions 8, 9 in folded back condition. In addition, after the crotch region 10 was folded onto the rear waist region 9, the pair of opposite lateral zones 11 have been connected to each other. It is possible thereby to keep the crotch region 10 in folded back condition. In this way, the used diaper 1 can be compactly folded up and kept in such condition in preparation for disposal. Thus it is possible to prevent the used diaper 1 from resulting in a bulky piece of garbage by compactly folding up the used diaper 1 and simultaneously to prevent the body waste and its malodor from leaking out by keeping the used diaper in folded up condition. Consequentially, the used diaper 1 can be disposed in a sanitary manner.

The waist elastic members 21 are attached to the chassis 2 so as to extend between the innermost side edges of the arrays of hook elements 15, 16 as viewed in the transverse direction X. With such arrangement, the used diaper 1 having been folded up can be sufficiently tightened to keep such folded up condition under the elastic force of the waist elastic members 21 as the lateral zones are folded back upon one another together with the hook elements 15, 16. The used diaper 1 is securely kept in such folded up condition and thereby body waste in this used diaper 1 is reliably prevented from leaking out. Particularly when the lateral zones are folded back onto each other so as to wrap the previously folded back crotch region 10, body waste discharged directly in the crotch region 10 can be held within the used diaper 1 having been folded up in this manner and body waste can be further reliably prevented from leaking out. The third engagement regions may be defined by the mount members 13, 14 to make it unnecessary to provide any dedicated means separately to fold up the used diaper and to keep the used diaper in such folded up condition. In consequence, an additional cost due to such dedicated means can be avoided.

While the lateral zone having the hook elements 16 is first folded back and then the lateral zone having the hook elements 15 is folded back according to this specific embodiment illustrated, it is obvious that this sequence may be inversed. While the front waist region 8 is provided with the hook elements and the rear waist region 9 is provided with the loop elements in this embodiment, it is also possible to provide the front waist region 8 with the loop elements and to provide the rear waist region 9 with hook elements. In other words, while the front waist region 8 has been described as the first waist region and the rear waist region 9 has been described as the second waist region, it is possible to define the rear waist region 9 as the first waist region and to define the front waist region 8 as the second waist region. In any case, it is important to attach the hook elements having a relatively high stiffness to the chassis 2 without a possibility that the hook elements might come in contact with the skin of the wearer and damage the skin. It is also possible to define the third engagement region by any one of the mount members 13, 14. However, the third engagement regions are preferably defined by both of the mount members 13, 14 so that the used diaper 1 can be properly folded up whether the lateral zone having the hook elements 15 is first folded back or the lateral zone having the hook elements 16 is first folded back. In this way, handling of the used diaper 1 is facilitated.

While, in accordance with the illustrated embodiment, both the front waist region 8 and the rear waist region 9 are elasticized by the waist elastic members 21, at least the waist region provided with the hook elements 15, 16 may be elasticized in order to assure that the used diaper 1 having been folded up can be kept in its compactly folded up condition. However, both the front waist region 8 and the rear waist region 9 are preferably elasticized to improve of the preventive effect against leak of body waste beyond the waist-opening 24. Furthermore, the number or the width dimension of rubber members forming the waist elastic members 21 in the vicinity of the waist-opening 24 may be increased or enlarged for further improvement of such leak-proof effect. While the liquid-absorbent core 20 is sandwiched between the inner and outer sheets 6, 7 forming the chassis 2 in the illustrated embodiment, the diaper 1 may comprise a liquid-absorbent structure including the liquid-absorbent core 20 separately of the chassis 2.

Although the hook elements 15, 16 are attached to the chassis 2 via the associated mount members 13, 14 in the illustrated embodiment, it is possible to attach the hook elements 15, 16 directly to the chassis 2. In such alternative embodiment, the hook elements 15, 16 may be attached to the outer sheet 7 in the front waist region 8 by adhesions or thermal or ultrasonic bonding means. When none of the mount members is used, regions of the inner sheet 6 facing the skin of the wearer corresponding to the inner side of the regions of the outer sheet 7 attached with the hook elements 15, 16 may define the third engagement regions. In this case, the inner sheet 6 should be formed of a fibrous sheet adapted to be engageable with the hook elements 15, 16.

For this alternative embodiment, it is unnecessary to provide the mount members 13, 14 and, in consequence, the cost of manufacturing can be correspondingly reduced. In addition, the inner sheet 6 defines the inner side of the chassis 2 facing the skin of the wearer and therefore the hook elements 15, 16 can be put in engagement with this inner side at any regions. In this way, the used diaper 1 can be adjustably folded up in a convenient manner.

The invention claimed is:
1. A wearing article and method of folding up the wearing article wherein the wearing article comprises:
 a chassis having longitudinal direction and transverse direction;
 an inner side facing the skin of a wearer and outer side facing a garment worn by the wearer;
 a first waist region defined by one of front and rear waist regions;
 a second waist region defined by the other of said front and rear waist regions;
 a crotch region extending between said first and second waist regions;
 a pair of first lateral zones of said first waist region which are opposed to each other in said transverse direction and extending in said longitudinal direction, each of said first lateral zones of said pair of first lateral zones consisting of first mechanical fastener engagement regions provided on a garment facing side surface thereof and third mechanical fastener engagement regions provided on a skin facing side surface thereof,
 a pair of second lateral zones of said second waist region which are opposed to each other in said transverse direction and extending in said longitudinal direction each of said second lateral zones of said pair of second lateral zones consisting of second mechanical fastener engagement regions providing on a skin facing side surface thereof,
 wherein said first mechanical fastener engagement regions include hook elements and said second mechanical fastener engagement regions include loop elements, whereby the first and second mechanical fastener engagement regions engage one another when the wearing article is worn by a user, and
 said first mechanical fastener engagement regions being engaged with said third mechanical fastener engagement regions when the wearing article is folded up after use for disposal;
 said first lateral zones include mount members via which said hook elements are attached to said first lateral zones and each said mount members respectively has an inner side of said mount member facing the skin of the wearer and an outer side facing the garment and formed of a fibrous sheet so that at least said inner side of said mount member facing the skin of the wearer is engageable with said hook elements and thereby defines said third engagement region; and the method of folding up said wearing article comprises the steps of:

detaching said first and second waist regions from each other along said first and second mechanical fastener engagement regions, placing said first and second waist regions upon each other with outer sides thereof exposed outside, folding back one of said first lateral zones onto said second waist region, folding back the other of said first lateral zones onto said second waist region so that said first mechanical fastener engagement region defined in said one of said first lateral zone is engaged with said third mechanical fastener engagement region defined on inner side of said first mechanical fastener engagement region defined in said other of said first lateral zones and thereby keeping the used diaper in its folded up condition;

wherein, in the folded up state, the hook elements disposed on said other of first lateral zones defines an uppermost layer of the wearing article.

2. The wearing article and method of folding up the wearing article as defined by claim 1, wherein the method of folding the wearing article further includes the steps of:

folding back said crotch region onto said second waist region before said step of folding back said one and said other of said first lateral zones onto said second waist region together with associated said second lateral zones, and interleaving said crotch region between said one and said other of said first lateral zones folded back together with associated said second lateral zones and said second waist region.

\* \* \* \* \*